United States Patent [19]
Hofmann

[11] Patent Number: 4,561,961
[45] Date of Patent: Dec. 31, 1985

[54] COOLED MICROSCOPE SLIDE AND ELECTRODE APPARATUS FOR USE IN LIVE CELL FUSION SYSTEM

[75] Inventor: Gunter A. Hofmann, San Diego, Calif.

[73] Assignee: Biotronics, San Diego, Calif.

[21] Appl. No.: 634,974

[22] Filed: Jul. 27, 1984

[51] Int. Cl.⁴ ............................................. B01D 57/02
[52] U.S. Cl. ............................. 204/299 R; 204/302; 204/308; 204/274; 204/289
[58] Field of Search ........... 204/271, 274, 289, 299 R, 204/302, 308

[56] References Cited

U.S. PATENT DOCUMENTS 4,326,934  4/1982  Pohl ................................. 204/180 R
4,441,972  4/1984  Pohl ................................. 204/299 R

OTHER PUBLICATIONS

Chen, C. S. et al., "Biological Dielectrophoresis: The Behavior of Lone Cells in a Nonuniform Electric Field", *Annals New York Acadamy of Sciences*, vol. 238, pp. 176–185, (1974).
Crane, J. S. et al., "Use of Balanced-Cell Technique to Determine Properties of Single Yeast Cells", *J. Biol. Phys.*, vol. 5, pp. 49–73, (1977).
Pohl, H. A. et al., "The Continuous Positive and Negative Dielectrophoresis of Microorganisms", *J. Biol. Phys.*, vol. 9, pp. 67–86, (1981).
D. E. P. Systems, Inc., brochure (1983), p. 4, "'Open' and 'Closed' Dielectrophoretic Fusion Slides".

*Primary Examiner*—Andrew H. Metz
*Assistant Examiner*—B. J. Boggs, Jr.
*Attorney, Agent, or Firm*—Baker, Maxham, Callan & Jester

[57] ABSTRACT

A glass slide has parallel tubular electrodes for performing electro cell fusion. Fluid may be pumped through the electrodes to dissipate heat to enhance the yield of viable hybrids. An alternate embodiment sandwiches a gasket and parallel tubular electrodes between glass slides to permit cell fusion in a closed sterile environment.

8 Claims, 3 Drawing Figures

COOLED MICROSCOPE SLIDE AND ELECTRODE APPARATUS FOR USE IN LIVE CELL FUSION SYSTEM

BACKGROUND OF THE INVENTION

The present invention relates to biological engineering, and more particularly, to a small scale device for holding live cells which may be fused by applying predetermined electric signals to the device.

The electro cell fusion process is generally done in several phases. In the first phase, the cells are brought close to each other to form pearl chains by exposing the cells to an alternating electric field. In the second phase, the cells which are in contact with each other are exposed for a brief moment to an alternating field of higher amplitude than the initial alternating electric field. The cells are pushed against each other and flatten out in the area of contact. In the third phase, cell fusion is initiated by one or more short, unidirectional pulses of high voltage. Under the correct conditions, pores in the cell membranes will open up and adjacent cells will fuse with each other. If the voltage is too high or the pulses too long, cell damage can occur and a non-viable hybrid results. There are particular parameters for optimal fusion yield for different cell types. In the fourth phase, the alignment alternating electric field is reapplied to maintain mechanical confinement and to aid in rounding off the fused cells.

Two physical processes are involved in the four phases of electro cell fusion. Dielectrophoresis governs the movement of the cells, i.e. alignment, compression and post fusion. Dielectric breakdown governs the actual fusion event.

Glass microscope slides have heretofore been provided with electrodes to enable small scale electro cell fusion. In some cases, the electrodes have taken the form of small wires extending across the top of the glass slide. Such a device is commercially available from GCA Corporation of Chicago, Ill. In another version, flat metal electrodes overlie the glass slide. Such a device is commercially available from D. E. P. Systems, Inc. of Metamora, Miss. In the foregoing devices, a droplet of fluid containing the cells to be fused is deposited on top of the electrodes and is held in place by capillary action. The construction of a small electro cell fusion device with a clear glass slide enables the four phases of the process to be observed through a microscope.

Other small electro cell fusion devices maintain the cell suspension fluid in a closed loop to permit repetitive sterile injection of fresh cells, with fused cells exiting the opposite end. Examples of this type of device are illustrated in FIG. 6 of U.S. Pat. No. 4,441,972. Another such device is called the "closed" design available from D. E. P. Systems, Inc.

SUMMARY OF THE INVENTION

Accordingly, it is the primary object of the present invention to provide an improved combination microscope slide and electrode device for use in a live cell fusion system.

Another object of the present invention is to provide a device of the aforementioned type which has a simple, durable construction adapted for repeated autoclaving and easy connection to a source of alternating current.

Still another object of the present invention is to provide a device of the aforementioned type which can produce a higher percentage of viable hybrids by dissipating the undesirable heat resulting from the applied electric fields.

Accordingly, the present invention provides a device in which stainless steel tubular electrodes extend across the surface of a glass microscope slide. The electrodes may be held in position by high temperature Epoxy. At one end of the glass slide, the electrodes may be bent upwardly and then curved over. This facilitates ready attachment of the alternating current power leads. Cooled liquid may be pumped through the hollow electrodes to dissipate heat. In a third version of the invention, a sealed chamber is provided by sandwiching a resilient, permeable seal between two plates. Stainless steel, tubular electrodes extend through the seal, and between the plates. Cell suspension fluid can be introduced into the chamber with a hypodermic needle inserted through the seal. Cooling fluid may also be pumped through the electrodes.

DESCRIPTION OF THE PREFERRED EMBODIMENTS

Figure 1:
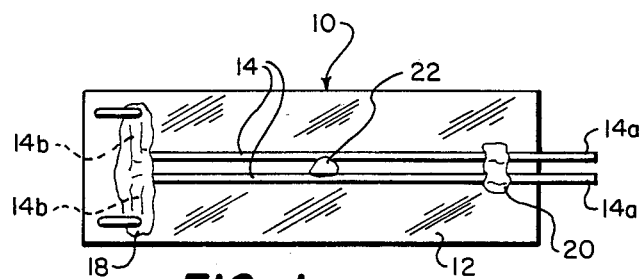
FIG. 1 is a top plan view of a first embodiment of my invention.

Referring to FIG. 1, the first embodiment 10 of my invention includes a rectangular, planar member 12 and a pair of parallel electrodes 14 which extend longitudinally on top of the planar member. Preferably, the phases of the electro cell fusion process may be observed through a microscope. Therefore, it is preferred that the planar member 12 be constructed of a material that is optically transparent. One suitable planar member is a conventional glass microscope slide.

It is important that the electrodes 14 have a particular cross-section. Cells in a fluid medium, when exposed to electric fields, generally behave like uncharged particles suspended in a liquid. The field induces charge separation in the cells. If the electric field is homogeneous, the cells will stay in place. However, if the electric field is inhomogeneous, such as that generated by electrodes with edges or a small radius, then the force of the electric field on the sides of the cells closer to the field concentration point (higher field strength) is larger than the force on the opposite sides of the cells. The result is that the cells move towards the field concentration area. Accordingly, an alternating (AC) electric field can be used to move the cells in one direction. When the cells come closer to the area of field concentration, they start being attracted to each other and form pearl chains of two or more cells.

Because of the foregoing, the electrodes 14 (FIG. 1) preferably have a round cross section and take the form of metal tubes. The reason for the tubular construction is that cooling liquids can then be pumped through the electrodes as described hereafter in conjunction with the second embodiment of FIG. 2. Stainless steel is preferred because of its strength and durability and because of its suitability for repeated sterilization through autoclaving. Electrodes 14 preferably have a small diameter, such as 0.030 inches or 0.75 millimeters. The gap or separation distance between the electrodes 14 should be small, and preferably the same as the diameter of the individual electrodes themselves. The spacing between the electrodes and the applied power, as well as the shapes of the electrodes determine the strength and gradient of the electric field therebetween.

Figure 2:
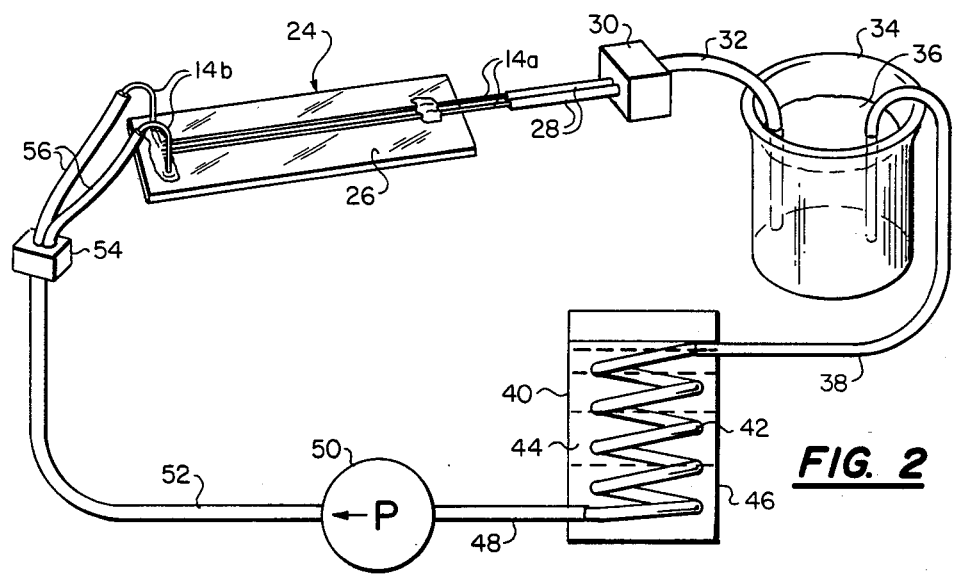
FIG. 2 is a perspective view of a second embodiment of my invention similar to the first embodiment and having a cooling fluid system connected thereto for dissipating excess heat resulting from the electric fields generated during electro cell fusion.

One set of ends 14a of the electrodes extend beyond one end of the planar member 12. The other set of ends 14b are bent at right angles and extend laterally on top of the planar member 12 and then upwardly, perpendicular to the planar member 12. As illustrated in FIG. 2, the terminal portions of the ends 14b of the electrodes are curved back toward the planar member 12. Alligator clips or other electric connection means may be readily attached to the upstanding end portions 14b of the electrodes. The curved terminal portions of the electrodes prevent the screening or other structure of an autoclave from being damaged during the sterilization process. As illustrated in FIG. 1, preferably the curved terminal portions of the ends 14b extend over the planar member 12, and not beyond the left end thereof. This reduces the likelihood that they will become inadvertently hooked on other structures and devices when autoclaved or transported.

The electrodes 14 may be attached to the planar member 12 by any suitable means that is simple and will withstand repeated autoclaving. Preferably, quantities 18 and 20 of a high temperature Epoxy bond the respective ends of electrodes to the planar member 12.

When the first embodiment 10 of my invention is utilized, a droplet 22 of a fluid with live cells suspended therein is deposited in the medial portion of the planar member 12 between and in contact with the electrodes 14. The device is then placed on a microscope, and leads from a controllable power source (not illustrated) are connected to the post ends 14b. Alternating currents and then current pulses may be applied to the electrodes to carry out the four phases of electro cell fusion described above.

In some cases, the generation of electric fields most desirable for accomplishing the cell alignment, cell compression and cell fusion, results in exposing the cells to excessive temperatures. If voltages are too high, or pulses too long, living cells can be damaged and non-viable hybrids will result. This can be avoided by providing a means for dissipating excess heat. The second embodiment 24 of my invention illustrated in FIG. 2 solves the foregoing problem. Specifically, a planar member and electrode combination 26 similar to the first embodiment 10 may have a cooling fluid pumped through its electrodes.

Referring now to specific details of the second embodiment illustrated in FIG. 2, pipes 28 connect the ends 14a of the electrodes to a manifold block 30. That block has passages for permitting the fluid to flow from the pipe 28 and into tubing 32 connected to the other side of the manifold block. The remote end of the tubing 32 drains into a reservoir 34 containing a quantity 36 of a suitable cooling fluid such as water. The intake end of another tubing 38 draws cooling fluid from the reservoir 34 through a heat exchange device 40 which may comprise a tubular coil 42 immersed in an ice bath 44 contained within a vessel 46. Another tubing 48 connects the outlet end of the coil 42 to a suitable pump 50 which conveys the cooling fluid through another tubing 52 into a second manifold block 54. Pipes 56 connect the second manifold block to the curved terminal ends 14b of the electrodes so that the cooling fluid may be pumped therethrough.

It will be understood by those skilled in the art that the cooling fluid delivery system described and illustrated in conjunction with FIG. 2 may be modified in many respects according to particular needs. An open loop fluid delivery system could be used instead of a closed loop, re-circulating system. Devices may be incorporated to control the rate of flow and to control the temperature of the cooling fluid. Furthermore, cooling fluids other than water may be desirable because of different thermodynamic characteristics. One alternate cooling fluid would be polyethylene glycol.

Figure 3:
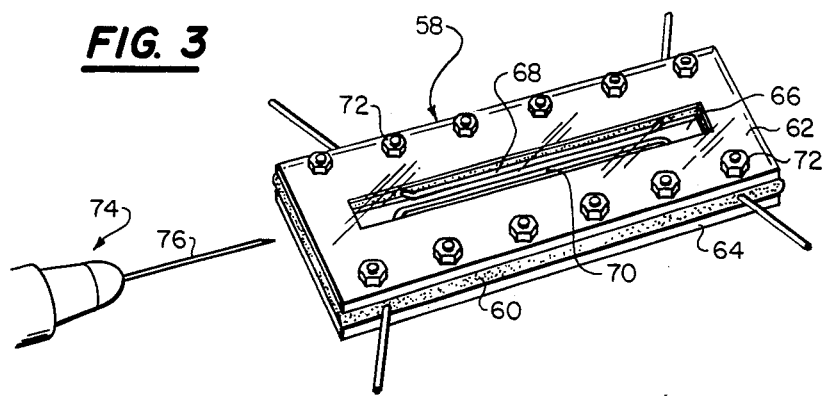
FIG. 3 is a perspective view of a third embodiment of my invention adapted for performing electro cell fusion in a sealed chamber.

FIG. 3 illustrates a third embodiment 58 of my invention adapted for performing electo cell fusion in a sealed chamber. A gasket or seal 60 is sandwiched between upper and lower planar members 62 and 64. The seal 60 is preferably made of high temperature resistant silicon rubber. The seal 60 has a rectangular cut-out in the medial portion thereof to define a chamber 66 between the members 62 and 64. Generally, C-shaped electrodes 68 and 70 have their straight middle segments positioned in parallel between the upper and lower members 62 and 64. The legs of the electrodes extend through the seal 60 beyond the peripheries of the members 62 and 64. The electrodes 68 and 70 are preferably made of stainless steel tubing of the same diameter as the electrodes 14 of my first embodiment. Preferably, the spacing between the parallel middle segments of the electrodes 68 and 70 is also the same as the spacing between electrodes 14 of my first embodiment.

The planar members 62 and 64 (FIG. 3) of my third embodiment are preferably high temperature resistant clear plastic. Means are provided for tightly securing the planar members around the gasket or seal 60 so that the chamber 66 is fluid tight. In the illustrated embodiment, these means comprise nut and bolt combinations 72 which extend through corresponding holes in the side edges of the planar members and seal.

The third embodiment of my invention may be used as follows. A fluid containing live cells in suspension may be injected into the chamber 66 from a hypodermic syringe 74. Needle 76 may be inserted through the end of the seal 60 into the chamber to inject the cell suspension fluid. A second needle (not illustrated) is inserted into the other end of the chamber to release air pressure. It may remain in place to allow flowthrough. The quantity of the cell suspension fluid and the placement thereof within the chamber 66 is such that the fluid contacts both electrodes 68 and 70. The apparatus 58 may then be placed on a microscope and power leads connected to the electrodes 68 and 70. The four phases of the electro cell fusion process may then be performed. If desired, cooling liquid may be pumped through the electrodes during the process in a manner analogous to that illustrated in FIG. 2. When the needles are withdrawn, the holes that were pierced in the seal squeeze shut so that the chamber 66 is fluid tight.

Instead of inserting and withdrawing the cell suspension fluid with hypodermic syringes, inlet and outlet ports in the end of the third embodiment 58 may be provided. These may be coupled to suitable pumps and reservoirs 44 to allow repeated injection of cells to be fused, and repeated withdrawal of resulting fused cells.

Having described preferred embodiments of my electro cell fusion microslide, modifications and adaptations thereof will occur to those skilled in the art. Accordingly, the protection afforded my invention should only be limited in accordance with the scope of the following claims.

I claim:

1. An apparatus for use in a live cell fusion system, comprising:
   a planar member;
   a pair of hollow tubular electrodes extending spaced apart and parallel along an upper surface of the planar member for having a predetermined set of electric currents from the cell fusion system applied thereto;
   means for securing the electrodes to the planar member; and
   means for conveying a cooling fluid through the hollow electrodes to dissipate heat generated by applying the predetermined set of electric currents to the electrodes.

2. An apparatus according to claim 1 wherein the electrodes have a round cross-section.

3. An apparatus according to claim 1 wherein the securing means comprises a high temperature resistant adhesive.

4. An apparatus according to claim 1 wherein a terminal portion of each electrode extends perpendicular from the upper surface of the planar member and curves back toward the upper surface.

5. An apparatus according to claim 1 wherein the electrodes have segments extending beyond a peripheral edge of the planar member.

6. An apparatus according to claim 1 wherein the electrodes are generally C-shaped, each including a straight first segment, and second and third end segments, and the apparatus further comprises:
   a second planar member;
   a planar fluid impervious seal having a central cut out region and made of an elastomeric material; and
   means for tightly securing the seal and electrodes between the planar members with the straight first segments of the electrodes positioned in the cut-out region and the second and third segments of the electrodes extending beyond the peripheral edges of the seal and the planar members.

7. An apparatus according to claim 1 wherein the planar member is made of an optically transparent material.

8. An apparatus according to claim 1 wherein the cooling fluid conveying means includes:
   a cooling fluid reservoir;
   a heat exchanger;
   a pump; and
   conduit means for coupling the reservoir, heat exchanger, pump and tubular electrodes so that the cooling fluid from the reservoir may be pumped through the heat exchanger to lower the temperature thereof and then through the electrodes.

* * * * *